United States Patent
Yehia et al.

(10) Patent No.: US 10,542,758 B1
(45) Date of Patent: Jan. 28, 2020

(54) METHANOL EXTRACT OF GRAPE SEED NANOPARTICLES

(71) Applicant: KING SAUD UNIVERSITY, Riyadh (SA)

(72) Inventors: Hany Mohamed Yehia, Cairo (EG); Reem Atta Alajmi, Riyadh (SA); Hatem Salama Mohamed Ali, Cairo (EG); Manal Fawzy Elkhadragy, Cairo (EG); Dina Mahmoud Metwally Hasanin, Zagazig (EG); Mohamed Fekry Serag El-Din, Shebin El-Kom (EG); Manal Ahmed Gasmelseed Awad, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/137,466

(22) Filed: Sep. 20, 2018

(51) Int. Cl.
*A01N 65/00* (2009.01)
*B01D 11/02* (2006.01)
*B82Y 40/00* (2011.01)

(52) U.S. Cl.
CPC .......... *A01N 65/00* (2013.01); *B01D 11/0288* (2013.01); *B82Y 40/00* (2013.01)

(58) Field of Classification Search
None
See application file for complete search history.

(56) References Cited

U.S. PATENT DOCUMENTS

| 9,061,049 | B2 | 6/2015 | Davies |
| 9,138,451 | B2 | 9/2015 | Popp |

FOREIGN PATENT DOCUMENTS

| CN | 101565414 A | * | 10/2009 |
| CN | 101597273 A | * | 12/2009 |
| CN | 101597273 A |   | 12/2009 |
| CN | 104855420 A |   | 8/2015 |
| CN | 105294636 A | * | 2/2016 |
| CN | 106176450 A |   | 12/2016 |
| CN | 106632206 A | * | 5/2017 |
| CN | 106753882 A |   | 5/2017 |

OTHER PUBLICATIONS

AZoM. Particle Size—US Sieve Series and Tyler Mesh Size Equivalents. Retrieved from the Internet on: Dec. 20, 2018. Retrieved from: <URL: https://www.azorn.com/article.aspx?ArticleID=1417>. (Year: 2018).*
Mirkarimi et al., "The Antimicrobial Activity of Grape Seed Extract againat Two Important Oral Pathogens", Zahedan J Res Med Sci (2013), vol. 15, No. 1, pp. 43-46.
Abdelbaky et al., "Nanoparticles Effects of Red Grade (Vitis vinifera) Seeds and Grape Seeds Powder on Obese Hyperlipidemic Rats", ARC Journal of Nutrition and Growth (2016), vol. 2, Iss. 2, pp. 1-15.
Jensen et al., "Rapid Extraction of Polyphenols from Red Grapes", Am.J. Enol. Vitic. (2007), vol. 58, No. 4, pp. 451-461.
Lorrain et al., "Evolution of Analysis of Polyphenols from Grapes, Wines, and Extracts", Molecules (2013), vol. 18, pp. 1076-1100.

* cited by examiner

*Primary Examiner* — Amy L Clark
(74) *Attorney, Agent, or Firm* — Richard C. Litman; Nath, Goldberg & Meyer

(57) ABSTRACT

The methanol extract of grape seed nanoparticles is prepared from grape seeds washed in distilled water and oven-dried at 60° C. for 12 hours. The seeds are milled or ground to a powder and sieved to a maximum size of 0.355 mm. The powder is added to concentrated HCl and stirred at 3000 rpm at 30° C. for one hour, and then distilled water is added with stirring for an additional 2 hours. The mixture is filtered, and the marc is dried to recover grape seed nanoparticles. The nanoparticles are added to methanol at the rate of 100 mg/ml, left in a shaker for 24 hours at room temperature, centrifuged, filtered, and the resulting extract (the supernatant) is recovered. Agar well diffusion testing showed that the nanoparticle extract exhibited greater antibacterial activity than a methanol extract of grape seeds alone, and testing showed greater antioxidant levels in the nanoparticle extract as well.

7 Claims, 3 Drawing Sheets

Micrococcus sp.

Salmonella typhimurium

Proteus sp.

Serratia marcescens

E. coli

Bacillus coagulans

Klebsiella pneumoniae

Listeria monocytogenes

Staph. aureus

Bacillus cereus

Bacillus subtilis

METHANOL EXTRACT OF GRAPE SEED NANOPARTICLES

BACKGROUND

1. Field

The disclosure of the present patent application relates to antibacterial agents and nanomaterials, and particularly to a methanol extract of grape seed nanoparticles and its antibacterial properties.

2. Description of the Related Art

Grape seed is a waste by-product of wine or juice making and a good source of functional compounds, such as polyphenols, which have broad potential applications as antioxidants. For example, grape seed proanthocyanidins were found to possess cardioprotective and nephroprotective abilities and can directly scavenge reactive oxygen species (ROS), including hydroxyl and peroxyl radicals.

Nanotechnology plays an increasingly crucial role in many key technologies of the new millennium. The application of nanoscale materials and structures, usually ranging from 1 to 100 nm, is an emerging area of nanoscience and nanotechnology. Nanoparticles show unique properties compared to bulk metals. Therefore, a lot of research work has been reported for the synthesis and applications of metal nanoparticles.

Various forms of bacteria, including both Gram-negative and Gram-positive bacteria, have been implicated in food poisoning and other forms of bacterial contamination. While antibacterial agents are known, various strains of bacteria have developed resistance to some conventional antibacterial agents, and there is always a perennial effort to find ways of increasing the strength and effectiveness of antibacterial agents.

Thus, a methanol extract of grape seed nanoparticles solving the aforementioned problems is desired.

SUMMARY

The methanol extract of grape seed nanoparticles is prepared from grape seeds washed in distilled water and oven-dried at 60° C. for 12 hours. The seeds are milled or ground to a powder and sieved to a maximum size of 0.355 mm. The powder is added to concentrated HCl and stirred at 3000 rpm at 30° C. for one hour, and then distilled water is added with stirring for an additional 2 hours. The mixture is centrifuged, and the marc is dried to recover grape seed nanoparticles. The nanoparticles are added to methanol at the rate of 100 mg/ml, left in a shaker for 24 hours at room temperature, centrifuged, filtered, and the resulting extract (the supernatant) is recovered. Agar well diffusion testing showed that the nanoparticle extract exhibited greater antibacterial activity than a methanol extract of grape seeds alone, and testing showed greater antioxidant levels in the nanoparticle extract as well.

These and other features of the present invention will become readily apparent upon further review of the following specification and drawings.

BRIEF DESCRIPTION OF THE DRAWINGS

FIG. 1B *Salmonella typhimurium*; FIG. 1C *Proteus* sp.; FIG. 1D *Serratia marcescens*; FIG. 1E *Escherichia coli*; FIG. 1F *Bacillua coagulans*; FIG. 1G *Klebsiella pneumoniae*; FIG. 1H *Listeria monocytogenes*; FIG. 1I *Staphylococcus aureus*; FIG. 1J *Bacillus cereus*; and FIG. 1J *Bacillus subtilis*, respectively.

Similar reference characters denote corresponding features consistently throughout the attached drawings.

DETAILED DESCRIPTION OF THE PREFERRED EMBODIMENTS

The methanol extract of grape seed nanoparticles is prepared from grape seeds washed in distilled water and oven-dried at 60° C. for 12 hours. The seeds are milled or ground to a powder and sieved to a maximum size of 0.355 mm. The powder is added to concentrated HCl and stirred at 3000 rpm at 30° C. for one hour, and then distilled water is added with stirring for an additional 2 hours. The mixture is centrifuged, and the marc is dried to recover grape seed nanoparticles. The nanoparticles are added to methanol at the rate of 100 mg/ml, left in a shaker for 24 hours at room temperature, centrifuged, filtered, and the resulting extract (the supernatant) is recovered. Agar well diffusion testing showed that the nanoparticle extract exhibited greater antibacterial activity than a methanol extract of grape seeds alone, and testing showed greater antioxidant levels in the nanoparticle extract as well.

The methanol extract of grape seed nanoparticles will be better understood with reference to the following examples.

Example 1

Preparation of Grape Seed Powder

Grape seeds (*Vitis vinifera* L.) were obtained from local markets in Riyadh Saudi Arabia. The seeds were washed with distilled water and then dried in an oven at 60° C. for 12 h. Samples were milled or ground to a powder and passed through a sieve of 0.355 mm (U.S.A Standard Sieve-ASTM-E 11) pore size and kept in a closed container.

Example 2

Preparation of Grape Seed Nanoparticles

Figure 1A:
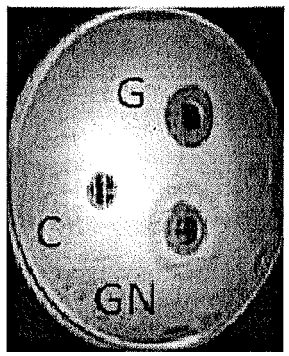
FIGS. 1A-1K are photographs of agar well diffusion assay results revealing the zone of inhibition of methanol extracts of grape seed nanoparticles (GN), methanol extracts of conventional grape seeds (G), and a methanol control (C) on bacteria strains of FIG. 1A *Micrococcus luteus*.
Figure 1B:
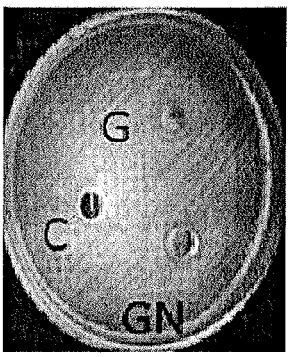
Figure 1C:
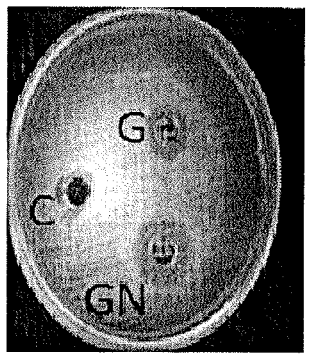
Figure 1D:
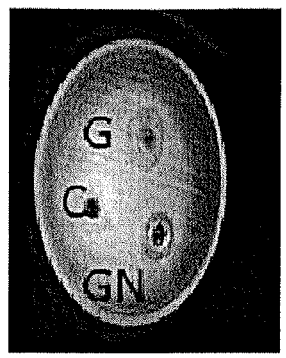
Figure 1E:
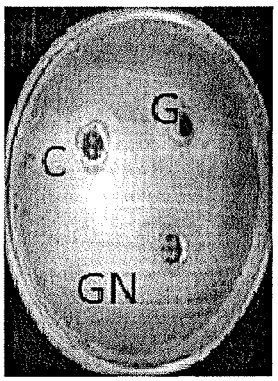
Figure 1F:
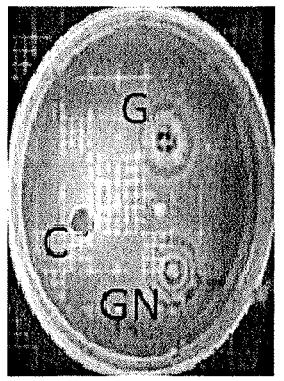
Figure 1G:
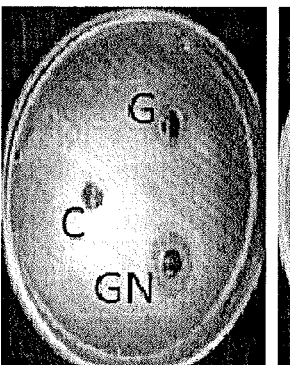
Figure 1H:
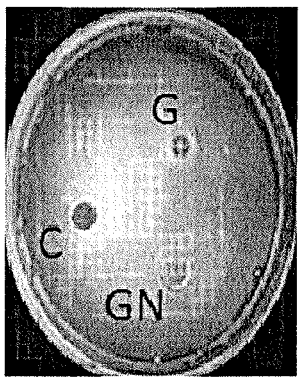
Figure 1I:
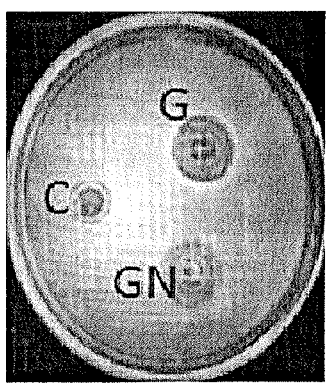
Figure 1J:
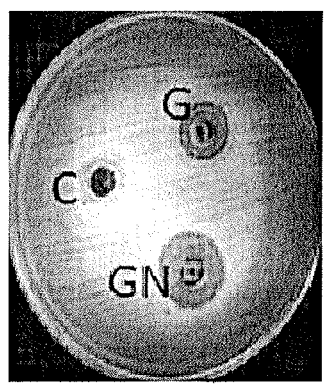
Figure 1K:
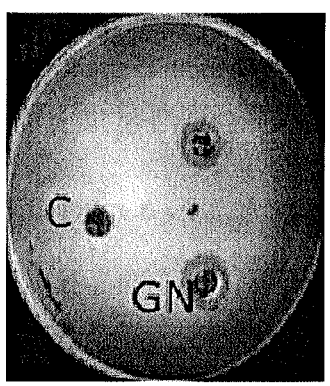
Figure 2A:
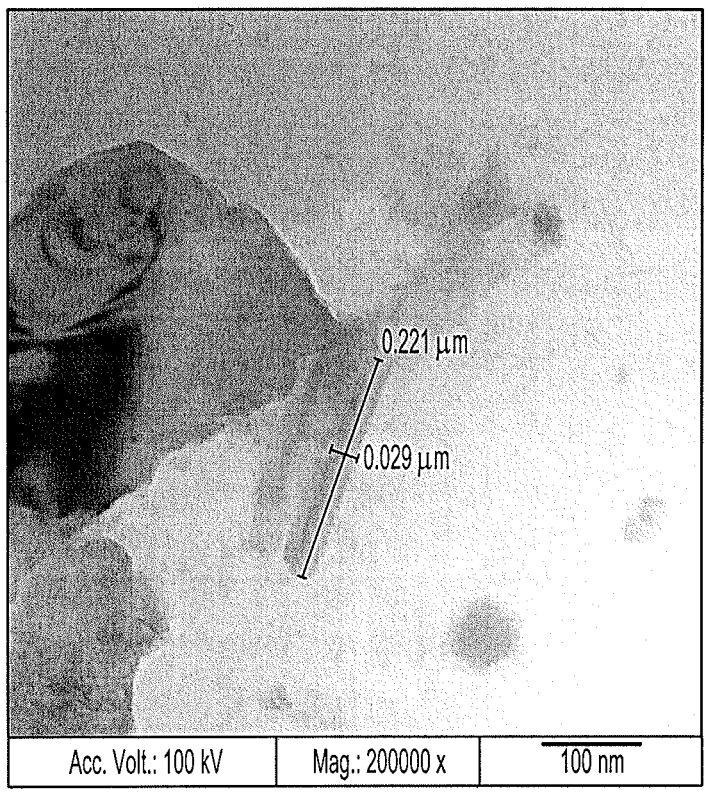
FIG. 2A is an exemplary transmission electron microscopy (TEM) photomicrograph of grape seed nanoparticles synthesized according to the present disclosure at 200000× magnification, showing a mixture of sheet and rod shapes of length 221 nm and width 29 nm.
Figure 2B:
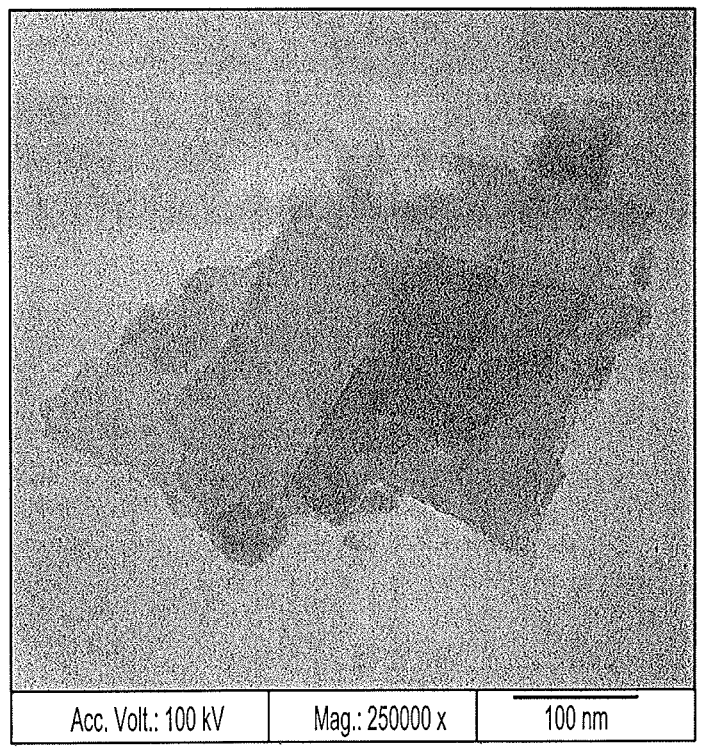
FIG. 2B is an exemplary transmission electron microscopy (TEM) photomicrograph of grape seed nanoparticles synthesized according to the present disclosure at 250000× magnification, showing a mixture of sheet shapes.
Figure 2C:
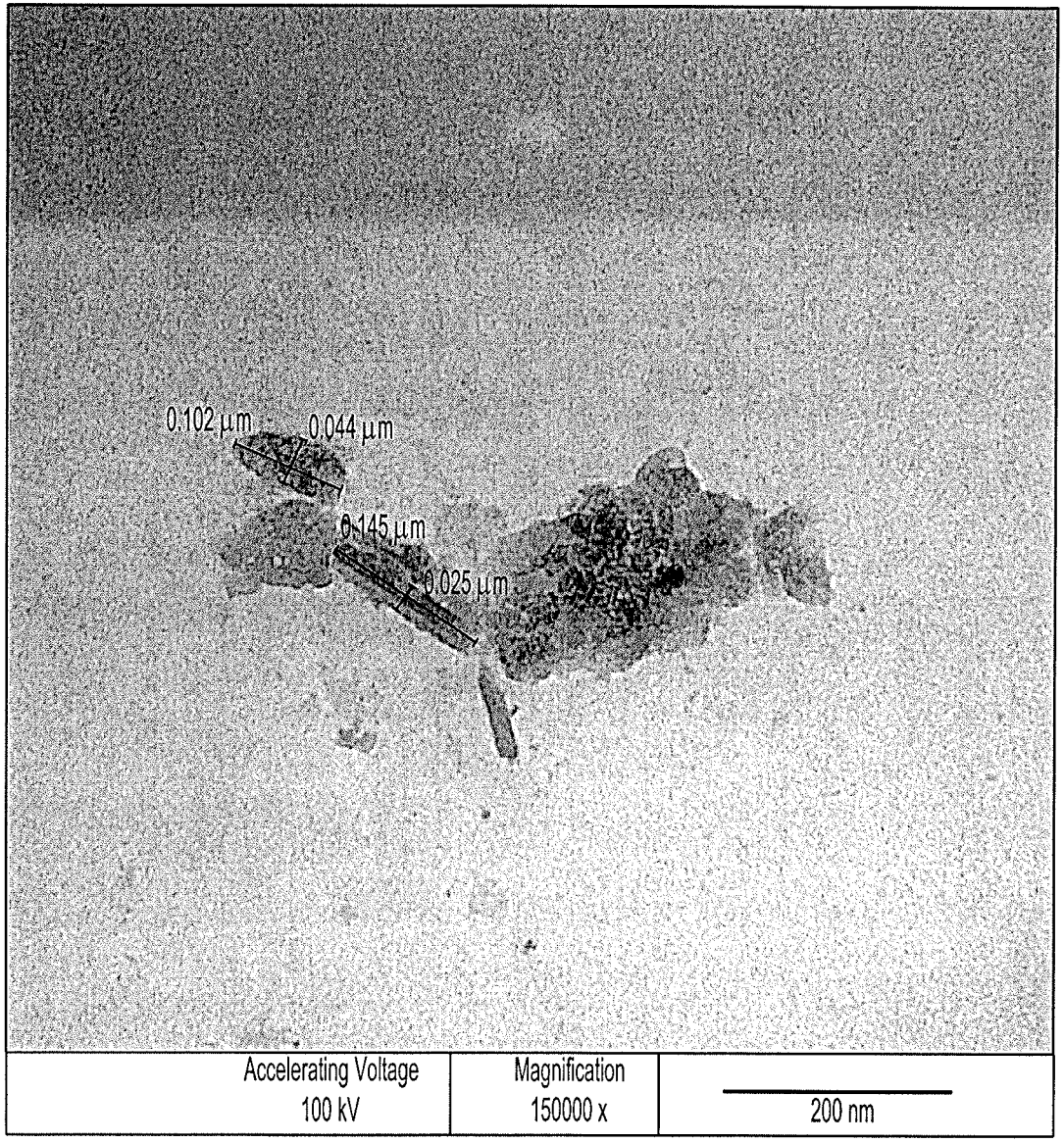
FIG. 2C is an exemplary transmission electron microscopy (TEM) photomicrograph of grape seed nanoparticles synthesized according to the present disclosure at 150000× magnification, showing a rod shapes of length 145 nm and width 25 nm and a smaller rod shape of length 102 nm and width of 44 nm.

About 0.4 g-0.7 g of grape seed powder was weighed and added to 30 ml of methanol and 3-5 ml of 38% hydrochloric acid and was kept under stirring for one hour at a temperature of 30° C. at a speed of 3000 rpm. Then, 30 ml of distilled water was added with continuous stirring for two more hours. The mixture was centrifuged at 9000 rpm for 15 minutes, and then filtered to collect the nanoparticles and dried. The grape seed nanoparticles were characterized by TEM micrographs (JEM-1400, JEOL, Japan), as shown in FIGS. 2A-2C, which showed a mixture of sheets and rod-shaped particles having lengths between about 100 to 250 nm and widths between about 25 to 45 nm.

Example 3

Agar Well Diffusion Assay

An agar well diffusion assay was used to determine the antimicrobial activity of methanol extracts of grape seed nanoparticles compared to methanol extracts of crude grape seed powder and a methanol control against common food-borne bacteria implicated in food poisoning and other forms of bacterial contamination, specifically: *Bacillua coagulans*, ATCC 7050; *Bacillus cereus*, ATCC 14579; *Bacillus subtilis*, local isolate; *Klebsiella pneumoniae*, ATCC 10031; *Micrococcus luteus*, local isolate; *Staphylococcus aureus*, ATCC 29737; *Listeria monocytogenes*, ATCC 19114; *Proteus* sp., local isolate; *Escherichia coli*, ATCC 10536; *Serratia marcescens*, local isolate; and *Salmonella typhimurium*, ATCC 14028. Each active bacterial strain was grown on Brain Heart Infusion agar (Oxoid CM 1136) for 24 h at 37° C. A sample from each bacterial strain on Brain Heart Infusion agar was then collected and diluted to a concentration of $10^6$ CFU/mL. 100 μL of each bacterial strain solution so prepared was spread on a Muller Hinton agar plate (Oxoid CM 0337), referred to hereinafter as the inoculated agar plate.

Methanol extracts of grape seed nanoparticles (the nanoparticles prepared as described in Example 2) and grape seeds (crude grape seed powder, prepared as in Example 1, above) were prepared by dissolving grape seed nanoparticles and grape seeds in 50 mL aliquots of methanol extraction solvent, respectively, at concentrations of 100 mg/ml. The mixtures were left on a shaker for 24 hours at room temperature. After that, the extraction mixtures were centrifuged at 10000 rpm for 15 minutes, and then filtered by Whatman No. 41 filter. The supernatant was adjusted to 50 ml by addition of methanol as needed, and kept in a freezer at −20° C. until needed. The extracts were used within one week.

Three holes were punched in each inoculated agar plate using a sterile cork borer with a diameter of 6 mm. A volume of 50 μL of methanol alone (C), 50 μL of methanol grape seed extract (G), and 50 μL of methanol grape seed nanoparticles extract (GN) was injected into each of the three holes, respectively, for each inoculated agar plate. The inoculated agar plates were then incubated at 37° C. for 24 h. The zone of inhibition was measured in mm for each strain tested. The results of this assay are illustrated in FIGS. 1A-1K and summarized in Table 1.

TABLE 1

Agar well diffusion assay results

| Tested Microorganisms | Zone of inhibition (mm) | |
|---|---|---|
| | Grape seed nanoparticles | Grape Seed |
| *Bacillua coagulans*, ATCC 7050, g+ | 15 | 15 |
| *Bacillus cereus*, ATCC 14579, g+ | 20 | 10 |

TABLE 1-continued

Agar well diffusion assay results

| Tested Microorganisms | Zone of inhibition (mm) | |
|---|---|---|
| | Grape seed nanoparticles | Grape Seed |
| *Bacillus subtilis*, local isolate, g+ | 15 | 8 |
| *Klebsiella pneumoniae*, ATCC 10031, g− | 20 | — |
| *Micrococcus luteus*, local isolate, g+ | 15 | 25 |
| *Staphylococcus aureus*, ATCC 29737, g+ | 20 | 20 |
| *Listeria monocytogenes*, ATCC 19114, g+ | — | — |
| *Proteus* sp., local isolate, g− | 25 | 8 |
| *Escherichia coli*, ATCC 10536, g− | — | — |
| *Serratia marcescens*, local isolate, g− | 15 | — |
| *Salmonella typhimurium*, ATCC 14028, g− | — | — |
| Effective ratio (% of C) | 72.7 | 54.5 |

It was found that the methanol extract of grape seed nanoparticles more effectively inhibits both Gram-positive and Gram-negative (g+ and g− in Table 1) bacteria relative to a methanol extract of crude grape seed powder. Some Gram negative bacteria, such as *Escherichia coli* ATCC 10536 and *Salmonella typhimurim* ATCC 14028, and also some Gram positive bacteria, such as *Listeria monocytogenes* ATCC 19114, were not affected by either grape seed nanoparticles or bulk grape seeds. The effective ratio of inhibition by grape seed nanoparticles was 72.7%, higher than 54.5% measured for bulk grape seed.

Without wishing to be bound by theory, it is thought that the grape seed nanoparticles present a greater surface area of grape seeds to the extraction solvent than the crude grape seed powder, resulting in more effective extraction of antioxidants from the grape seeds and a higher concentration of antioxidants in the extract, volume:volume, and therefore more potent antibacterial activity from the grape seed nanoparticle extract, given the same volume of extract.

Example 4

Determination of Total Phenolic Compounds and Total Flavonoids

The total content of phenolic compounds in the methanol extract of grape seed nanoparticles and the methanol extract of grape seeds, respectively, was determined by the Folin-Ciocalteu method. For example, a volume of 2.5 ml of distilled water and 0.1 ml of a sample extract were added to a test tube, followed by addition of 0.1 ml of undiluted commercially available Folin-Ciocalteu reagent (Sigma-Aldrich, St. Louis, Mo., USA). The solution was mixed well and then allowed to stand for 6 min before 0.5 ml of a 20% sodium carbonate solution was added. The color was developed during 30 min at room temperature (around 20° C.), and the absorbance at 760 nm was measured using a spectrophotometer (Milton Roy Spectronic 1201, USA). A blank sample was prepared using 0.1 ml of methanol, instead of extract. The measurement was compared to a calibration curve of gallic acid solutions and expressed as gallic acid equivalents per gram of dry weight sample.

The total flavonoid content in the methanol extract of grape seed nanoparticles and the methanol extract of grape seeds, respectively, were determined by the aluminum chloride colorimetric method. In brief, 50 μL of a sample extract was mixed with 4 mL of distilled water, followed by 0.3 mL of 5% $NaNO_2$ solution. After 5 minutes, 0.3 mL of 10% $AlCl_3$ solution was added, and the mixture was allowed to stand for 6 min. Then, 2 mL of 1 mol/L NaOH solution was added, and the final volume of the mixture was brought to 10 mL with distilled water. The mixture was allowed to stand for 15 min, and absorbance at 510 nm was measured using a spectrophotometer. The total flavonoid content was calculated from a calibration curve, and the result was expressed as mg rutin equivalent per g dry weight or mg catechin equivalent per g dry weight.

The results for total phenols and total flavonoids are presented in Table 2, as follows.

TABLE 2

Total phenols and total flavonoids in methanol extracts

| Sample | Total phenols (mg Gallic acid/ g sample) | Total flavonoids (mg catechin/g sample) | Total flavonoids (mg rutin/g sample) |
|---|---|---|---|
| Grape seed | 18.906 ± 0.319 | 0.456 ± 0.004 | 4.867 ± 0.046 |
| Grape seed nanoparticles | 1148.692 ± 13.960 | 24.738 ± 0.418 | 264.701 ± 4.618 |

Results expressed as mean ± standard deviation

Example 5

Testing for DPPH (2,2-diphenyl-1-picrylhydrazyl) Radical Scavenging Activity

The ability of the methanol extract of grape seed nanoparticles and the methanol extract of grape seeds, respectively, to scavenge DPPH radicals was determined as follows. A 0.08 mM DPPH radical stock solution in methanol was prepared, and 950 μL of DPPH stock solution was added to 50 μL of each extract and incubated for 5 min. At exactly 5 minutes after mixing, absorbance at 510 nm was measured for each mixture using a spectrophotometer (Cary 50 Scan; Varian). Antioxidant activity (AA) was expressed as a percentage inhibition of DPPH radical calculated according to the following equation:

$$AA=100-[100\times(A_{sample}/A_{control})]$$

where $A_{sample}$ is the absorbance of the sample at t=5 min, and $A_{control}$ is the absorbance of a control of pure methanol. The results are presented in Table 3, below.

Example 6

Testing of ABTS (2,2'-azinobis-(3-ethylbenzothiazoline-6-sulfonate)) Radical Scavenging Activity The ABTS assay, or Trolox equivalent antioxidant capacity (TEAC) assay, was performed as follows. A solution of the ABTS radical cation, ABTS.+, (referred to herein as "the ABTS radical cation solution") was prepared by reacting 50 mL of 2 mM ABTS solution with 200 μL of 70 mM potassium persulfate solution. This mixture was stored in the dark for 16 h at room temperature. For each methanol extract, the ABTS radical cation solution was diluted with pH 7.4 phosphate buffered saline (PBS) solution to an initial absorbance of 0.700±0.021 at 734 nm by spectrophotometer. This solution was newly prepared for each set being analyzed. To determine the antiradical scavenging activity, 100 μL of the sample methanol extract or of the control (pure methanol) was added to 1.8 mL of the ABTS radical cation solution and the change in absorbance measured at a 734 nm was recorded over 6 min. Results were expressed as μmol Trolox equivalent per g of dried sample (μmol eq. Trolox/g), based on a Trolox calibration curve. The results are presented in Table 3, below.

Example 7

Ferric Reducing Antioxidant Power (FRAP)

Testing for ferric reducing antioxidant power (FRAP) was performed as follows. The FRAP reagent included 300 mM acetate buffer, pH 3.6, 10 mM TPTZ (2,4,6-tri(2-pyridyl)-s-triazine) in 40 mM HCl, and 20 mM $FeCl_3$ in a ratio of 10:1:1 (v/v/v). Three ml of the FRAP reagent was mixed with 100 μL of the sample methanol extract in a test tube and vortexed in the incubator at 37° C. for 30 min in a water bath. Reduction of ferric-tripyridyltriazine to ferrous complex resulted in an intense blue color, which was measured using a UV-Vis spectrophotometer (Cary 50 Scan; Varian) at 593 nm at 4 min. after mixing with the sample methanol extract. Results were expressed in terms of μmol Trolox equivalent per g of dried sample (μmol eq. Trolox/g). The results are presented in Table 3, below.

TABLE 3

Results of DPPH, ABTS, and FRAP testing

| Sample | DPPH (%) | ABTS (mmol Trolox/g sample) | FRAP (mmol Trolox/g sample |
|---|---|---|---|
| Grape seed | 37.99 ± 1.768 | 1.085 ± 0.061 | 1.052 ± 0.003 |
| Grape seed nanoparticles | 85.784 ± 0.212 | 63.428 ± 0.264 | 65.546 ± 1.935 |

Results expressed as mean ± standard deviation

It is to be understood that the synthesis of grape seed nanoparticles and their use as an antibacterial agent is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making a methanol extract of grape seed nanoparticles for use as an antibacterial agent, comprising the steps of:
   grinding grape seeds to form a crude grape seed powder, wherein the step of grinding grape seeds comprises:
   i) washing the grape seeds in distilled water;
   ii) oven-drying the washed grape seeds for 12 hours;
   iii) grinding the washed and oven-dried grape seeds; and
   iv) sieving the ground grape seeds through a sieve having a pore size of 0.355 mm;
   converting the crude grape seed powder into grape seed nanoparticles, wherein the step of converting the crude grape seed powder into grape seed nanoparticles comprises:
   a) mixing the crude grape seed powder with concentrated hydrochloric acid;
   b) stirring the mixture of crude grape seed powder with concentrated hydrochloric acid for one hour;
   c) adding distilled water to the stirred mixture of crude grape seed powder with concentrated hydrochloric acid;

d) stirring the mixture for an additional two hours after adding the distilled water to obtain grape seed nanoparticles in solution;

e) filtering the grape seed nanoparticles in solution to isolate the grape seed nanoparticles from the solution; and f) drying the isolated grape seed nanoparticles; and extracting the grape seed nanoparticles in methanol to form the methanol extract of grape seed nanoparticles, wherein said step of extracting the grape seed nanoparticles in methanol comprises the steps of:

1) dissolving the grape seed nanoparticles in methanol at a concentration of 100 mg/ml to form an extraction mixture;

2) leaving the extraction mixture on a shaker for 24 hours at room temperature;

3) centrifuging the extraction mixture at 10000 rpm for 15 minutes;

4) filtering the extraction mixture; and 5) retaining supernatant from the filtered extraction mixture as the methanol extract of grape seed nanoparticles.

2. The method of making a methanol extract of grape seed nanoparticles according to claim 1, wherein said step of oven-drying the washed grape seeds comprises drying the grape seeds in an oven at 60° C.

3. The method of making a methanol extract of grape seed nanoparticles according to claim 1, wherein said concentrated hydrochloric acid comprises 38% HCl w/w.

4. The method of making a methanol extract of grape seed nanoparticles according to claim 1, wherein said step of stirring the mixture of crude grape seed powder with concentrated hydrochloric acid comprises stirring the mixture at 3000 rpm for one hour.

5. The method of making a methanol extract of grape seed nanoparticles according to claim 1, wherein said step of stirring the mixture of crude grape seed powder with concentrated hydrochloric acid comprises stirring the mixture at a temperature of about 30° C.

6. The method of making a methanol extract of grape seed nanoparticles according to claim 1, wherein said step of drying the isolated grape seed nanoparticles comprises drying the isolated grape seed nanoparticles at 35° C.

7. The method of making a methanol extract of grape seed nanoparticles according to claim 1, wherein said isolated grape seed nanoparticles have a length between about 100 to 250 nm and width between about 25 to 45 nm.

* * * * *